(12) United States Patent
Bristol

(10) Patent No.: US 8,253,942 B2
(45) Date of Patent: Aug. 28, 2012

(54) OPTICAL GAS DETECTOR

(75) Inventor: L. Rodney Bristol, Chalfont, PA (US)

(73) Assignee: Scott Technologies, Inc., Boca Raton, FL (US)

( * ) Notice: Subject to any disclaimer, the term of this patent is extended or adjusted under 35 U.S.C. 154(b) by 875 days.

(21) Appl. No.: 11/862,959

(22) Filed: Sep. 27, 2007

(65) Prior Publication Data

US 2009/0086191 A1 Apr. 2, 2009

(51) Int. Cl.
*G01N 21/00* (2006.01)
(52) U.S. Cl. .................................................... 356/437
(58) Field of Classification Search .................. None
See application file for complete search history.

(56) References Cited

U.S. PATENT DOCUMENTS

| | | | |
|---|---|---|---|
| 4,176,963 A * | 12/1979 | Fabinski et al. ............... | 356/435 |
| 4,471,220 A * | 9/1984 | Perry et al. ............... | 250/339.04 |
| 4,507,558 A * | 3/1985 | Bonne ............................ | 250/345 |
| 5,091,649 A | 2/1992 | Rantala | |
| 5,095,913 A | 3/1992 | Yelderman et al. | |
| 5,202,570 A | 4/1993 | Tanaka et al. | |
| 5,281,816 A | 1/1994 | Jacobson et al. | |
| 5,313,406 A | 5/1994 | Kauppinen et al. | |
| 5,418,366 A | 5/1995 | Rubin | |
| 5,448,070 A | 9/1995 | Day et al. | |
| 5,475,222 A | 12/1995 | King | |
| 5,506,149 A | 4/1996 | Crawford et al. | |
| 5,508,525 A | 4/1996 | Day et al. | |
| 5,546,804 A | 8/1996 | Johnson et al. | |
| 5,550,636 A * | 8/1996 | Hagans et al. ................ | 356/437 |
| 5,585,636 A | 12/1996 | Dollansky | |
| 5,608,219 A | 3/1997 | Aucremanne | |
| 5,886,247 A * | 3/1999 | Rabbett ........................ | 356/437 |
| 5,886,348 A | 3/1999 | Lessure et al. | |
| 5,933,792 A | 8/1999 | Andersen et al. | |
| 6,002,133 A | 12/1999 | Nelson et al. | |
| 6,008,928 A * | 12/1999 | Sachse et al. ................. | 359/246 |
| 6,010,665 A | 1/2000 | Dosoretz et al. | |
| 6,061,141 A | 5/2000 | Goldenberg et al. | |
| 6,108,096 A | 8/2000 | Ushio et al. | |

(Continued)

FOREIGN PATENT DOCUMENTS

EP 256314 A2 * 2/1988

(Continued)

*Primary Examiner* — Gregory J Toatley
*Assistant Examiner* — Juan D Valentin
(74) *Attorney, Agent, or Firm* — Charles H. Livingston; The Small Patent Law Group LLC

(57) ABSTRACT

A gas detector is provided. The gas detector includes a measurement source of optical radiation, a reference source of optical radiation, a measurement detector configured to provide an output signal indicative of a gas of interest, a reference detector configured to provide an output signal at least partially independent of the gas of interest, a measurement optical path extending from the measurement source to the reference and measurement detectors, and a sample region for receiving a gaseous sample. The sample region is located along the measurement optical path. A window is positioned in the measurement optical path downstream from the measurement source and upstream from the reference and measurement detectors. The window is partially transparent to optical radiation and partially reflective to optical radiation. The window is positioned to either reflect a portion of the optical radiation emitted by the reference source into the measurement optical path or to allow a portion of the optical radiation emitted by the reference source to pass through the window into the measurement optical path.

2 Claims, 10 Drawing Sheets

U.S. PATENT DOCUMENTS

| | | | |
|---|---|---|---|
| 6,196,046 B1 | 3/2001 | Braig et al. | |
| 6,252,668 B1 * | 6/2001 | Hill | 356/487 |
| 6,267,928 B1 | 7/2001 | Yamamori et al. | |
| 6,362,004 B1 | 3/2002 | Noblett | |
| 6,387,709 B1 | 5/2002 | Mason et al. | |
| 6,396,056 B1 | 5/2002 | Lord et al. | |
| 6,410,918 B1 | 6/2002 | Kouznettsov | |
| 6,414,310 B1 | 7/2002 | Smith | |
| 6,519,039 B1 * | 2/2003 | Morishita et al. | 356/437 |
| 6,545,278 B1 | 4/2003 | Mottier et al. | |
| 6,555,820 B1 | 4/2003 | Tacke et al. | |
| 6,642,521 B2 | 11/2003 | Namose et al. | |
| 6,687,005 B2 | 2/2004 | Kim | |
| 6,741,181 B2 | 5/2004 | Skaggs | |
| 6,775,001 B2 | 8/2004 | Friberg et al. | |
| 6,791,689 B1 * | 9/2004 | Weckstrom | 356/437 |
| 6,825,471 B1 | 11/2004 | Shulga et al. | |
| 6,836,523 B2 | 12/2004 | Izumi et al. | |
| 6,858,846 B2 | 2/2005 | Hjertman | |
| 6,918,281 B2 | 7/2005 | Sussman et al. | |
| 6,943,884 B2 | 9/2005 | Rice | |
| 7,057,164 B2 | 6/2006 | Springsteen et al. | |
| 7,061,608 B2 | 6/2006 | Bradshaw | |
| 7,132,657 B2 | 11/2006 | Smith | |
| 7,146,841 B2 | 12/2006 | Forrest | |
| 7,148,488 B2 | 12/2006 | Horton et al. | |
| 7,166,842 B2 | 1/2007 | Minuth et al. | |
| 7,193,718 B2 * | 3/2007 | Lundqvist et al. | 356/437 |
| 7,216,544 B2 | 5/2007 | Vaccaro et al. | |
| 7,230,709 B2 | 6/2007 | Kusuda | |
| 7,274,453 B2 | 9/2007 | Sottery et al. | |
| 7,291,849 B1 | 11/2007 | Baiocchi et al. | |
| 7,352,463 B2 * | 4/2008 | Bounaix | 356/437 |
| 2003/0111607 A1 | 6/2003 | Bachur, Jr. et al. | |
| 2004/0147034 A1 | 7/2004 | Gore et al. | |
| 2004/0227937 A1 | 11/2004 | Richardson | |
| 2005/0094149 A1 * | 5/2005 | Cannon | 356/437 |
| 2005/0217370 A1 | 10/2005 | Takahashi et al. | |
| 2005/0286054 A1 * | 12/2005 | Chen et al. | 356/437 |
| 2006/0156789 A1 | 7/2006 | Frank et al. | |
| 2006/0219923 A1 | 10/2006 | Uchida et al. | |
| 2006/0239402 A1 | 10/2006 | Hu et al. | |
| 2006/0262311 A1 * | 11/2006 | Muta et al. | 356/437 |
| 2007/0023670 A1 | 2/2007 | Glover | |
| 2007/0062249 A1 | 3/2007 | Forrest | |
| 2007/0146715 A1 | 6/2007 | Potyrailo et al. | |
| 2007/0229834 A1 | 10/2007 | Patel et al. | |

FOREIGN PATENT DOCUMENTS

JP            01009341 A    *   1/1989

* cited by examiner

OPTICAL GAS DETECTOR

BACKGROUND OF THE INVENTION

The invention relates generally to gas detectors, and, more particularly, to optical gas detectors.

Gas detectors are often used to detect a gas of interest under various conditions and in a variety of environments. For example, gas detectors may be used to monitor ambient air for the presence of flammable gases to protect firefighters or other emergency workers. Optical gas detectors are one type of gas detector that uses optical radiation to detect the presence and the concentration of a gas of interest. Specifically, optical radiation can cause gas molecules to oscillate. The oscillating molecules draw energy from the optical radiation and therefore absorb a portion of the optical radiation. The amount of radiation absorbed by the gas can be used to determine the presence and concentration of the gas of interest in the ambient air. Typically, an optical radiation source is used to emit optical radiation into a sample region containing a gaseous sample from the ambient air. A reduction of the intensity of the optical radiation due to the absorption of optical radiation by the gaseous sample is then detected at a detector positioned downstream from the sample region.

Early optical gas detectors typically include only a single radiation source and only a single detector. However, optical gas detectors that include only a single detector and only a single optical radiation source may only be able to provide reliable and unambiguous measurements under generally stable ambient conditions. Any change in the intensity of the optical radiation emitted by the optical radiation source, for example due to contaminants such as dust and/or a change in temperature and/or humidity, would appear to indicate the presence of the gas of interest. To overcome the measurement inaccuracies of early optical gas detectors, a second detector, referred to as a reference detector, may be used to carry out a parallel measurement of the radiation intensity at a different wavelength than the first detector, which is referred to as a measurement detector. The different wavelength is selected as a wavelength that will not be absorbed by the gas of interest, thereby providing a reference measurement that can be cross-calculated with the measurement of the measurement detector to provide a measure of the actual concentration of the gas of interest.

To further increase accuracy, a second, or reference radiation source may be used to provide four measurements instead of only two, sometimes referred to as "double-compensated" optical gas detectors. Specifically, the first, or measurement radiation source and the reference radiation source are arranged such that they emit radiation at different times or are modulated at two different frequencies. The optical radiation emitted from the measurement radiation source passes through the sample region, while the optical radiation emitted from the reference radiation source does not pass through the sample region. Accordingly, both detectors will receive an additional signal from the reference radiation source that is not affected by the gaseous sample. The additional signals provided by the reference radiation source serve as a measure of the relative sensitivity of each detector under the prevailing ambient conditions.

At least some known double-compensated optical gas detectors include a beam splitter positioned to direct radiation emitted from each of the radiation sources to both of the detectors. Specifically, the beam splitter is positioned relative to the reference radiation source such that a portion of the optical radiation emitted from the reference radiation source travels through the beam splitter to one of the detectors and another portion of the optical radiation emitted from the reference radiation source is reflected by the beam splitter to the other detector. In contrast, the detector that receives reference radiation reflected from the beam splitter receives radiation emitted from the measurement radiation source that has traveled through the beam splitter, while the detector that receives reference radiation that has traveled through the beam splitter receives measurement radiation that has been reflected from the beam splitter. However, changes in ambient conditions, for example due to contaminants such as dust and/or a change in temperature and/or humidity, may cause the beam splitter ratio to change. This may be a result of a change in the index of refraction and/or a change in the ratio of reflective area to transmissive area of the splitter. In a known arrangement, where the reference radiation and the measurement radiation are reflected from opposite sides of the splitter and where the transmitted portion of each radiation stimulates opposite detectors (of the reference and measurement pair of detectors), any change in beam splitter ratio affects the detectors inversely, which may be indistinguishable from a change in concentration of the gas of interest.

There is a need for an optical gas detector that is less sensitive to changing ambient conditions.

BRIEF DESCRIPTION OF THE INVENTION

In one embodiment, a gas detector is provided. The gas detector includes a measurement source of optical radiation, a reference source of optical radiation, a measurement detector configured to provide an output signal indicative of a gas of interest, a reference detector configured to provide an output signal at least partially independent of the gas of interest, a measurement optical path extending from the measurement source to the reference and measurement detectors, and a sample region for receiving a gaseous sample. The sample region is located along the measurement optical path. A window is positioned in the measurement optical path downstream from the measurement source and upstream from the reference and measurement detectors. The window is partially transparent to optical radiation and partially reflective to optical radiation. The window is positioned to either reflect a portion of the optical radiation emitted by the reference source into the measurement optical path or to allow a portion of the optical radiation emitted by the reference source to pass through the window into the measurement optical path.

Optionally, the gas detector includes a beam splitter configured to direct a portion of optical radiation emitted from the measurement source to the measurement detector and another portion of optical radiation emitted from the measurement source to the reference detector. The beam splitter is configured to direct a portion of optical radiation emitted from the reference source to the measurement detector and another portion of optical radiation emitted from the reference source to the reference detector.

Optionally, the portion of the measurement optical path from the measurement source through the sample region is approximately straight.

In another embodiment, a gas detector is provided. The gas detector includes a measurement source of optical radiation, a reference source of optical radiation, and a beam splitter partially transparent to optical radiation and partially reflective to optical radiation. The beam splitter has a first side and an opposite second side. The first side is positioned to receive optical radiation from both the measurement source and the reference source.

In another embodiment, a gas detector is provided. The gas detector includes a measurement source of optical radiation, a reference source of optical radiation, a measurement detector configured to provide an output signal indicative of a gas of interest, a reference detector configured to provide an output signal at least partially independent of the gas of interest, and a beam splitter partially transparent to optical radiation and partially reflective to optical radiation. The beam splitter is configured to allow a portion of the optical radiation emitted by both the reference and measurement sources to pass therethrough to the measurement detector or the reference detector. The beam splitter is configured to reflect a portion of the optical radiation emitted by both the reference and measurement sources to the other of the measurement and reference detectors.

In another embodiment, a method is provided for detecting a gas of interest using a sample region having a gaseous sample therein. The method includes transmitting optical radiation from a measurement source along a measurement optical path extending from the measurement source, through the sample region, and to a measurement detector and a reference detector, and transmitting optical radiation from a reference source to a window that either reflects a portion of the optical radiation emitted by the reference source into the measurement optical path or allows a portion of the optical radiation emitted by the reference source to pass through the window into the measurement optical path.

DETAILED DESCRIPTION OF THE INVENTION

As used herein, the term "optical radiation" is intended to mean electromagnetic radiation in the wavelength range of approximately 100 nm to approximately 1 mm (e.g., the ultraviolet, visible, and infrared radiations).

Figure 1:
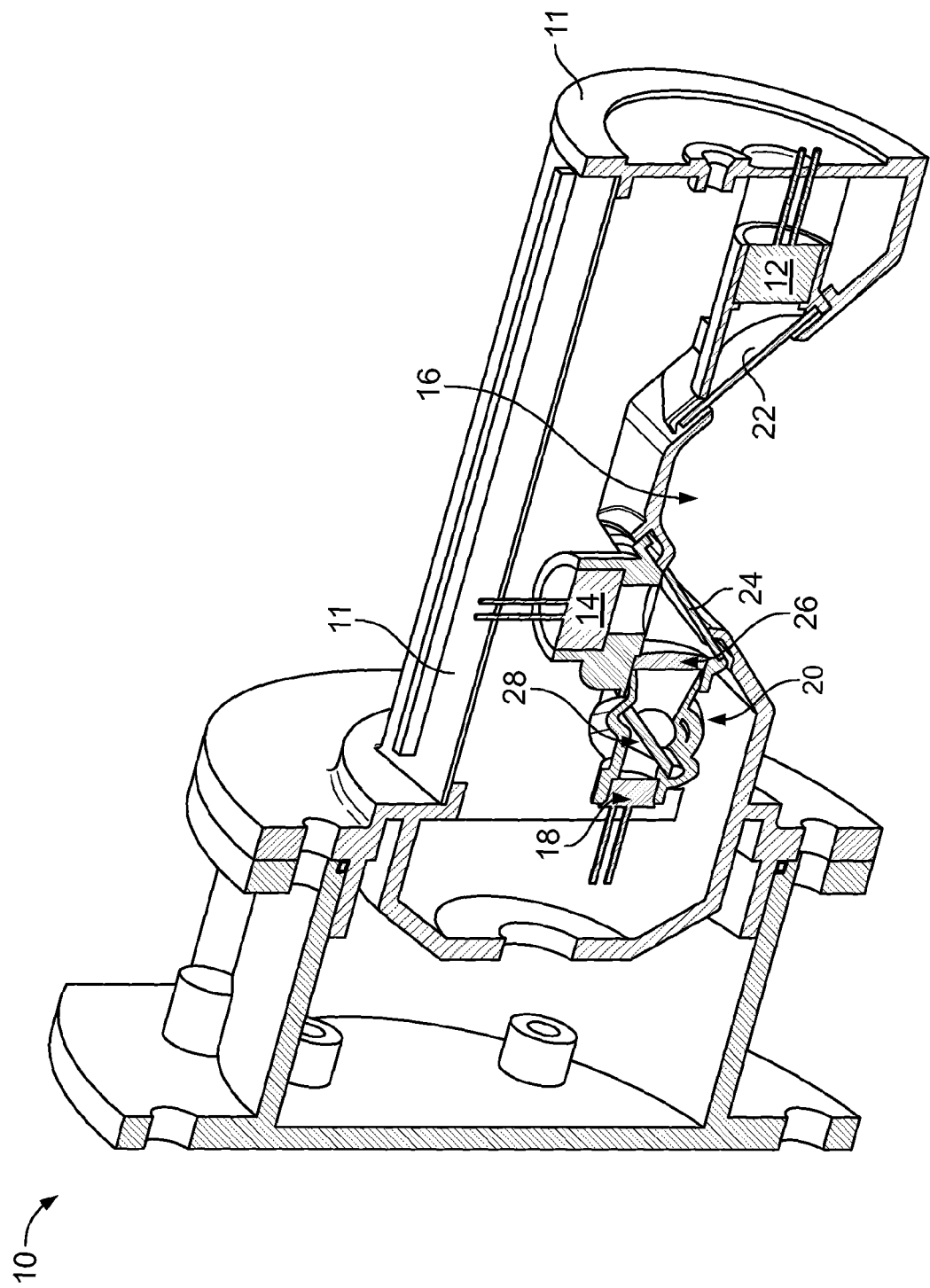
FIG. 1 is a perspective view of a cross section of an exemplary embodiment of an optical gas detector.
Figure 2:
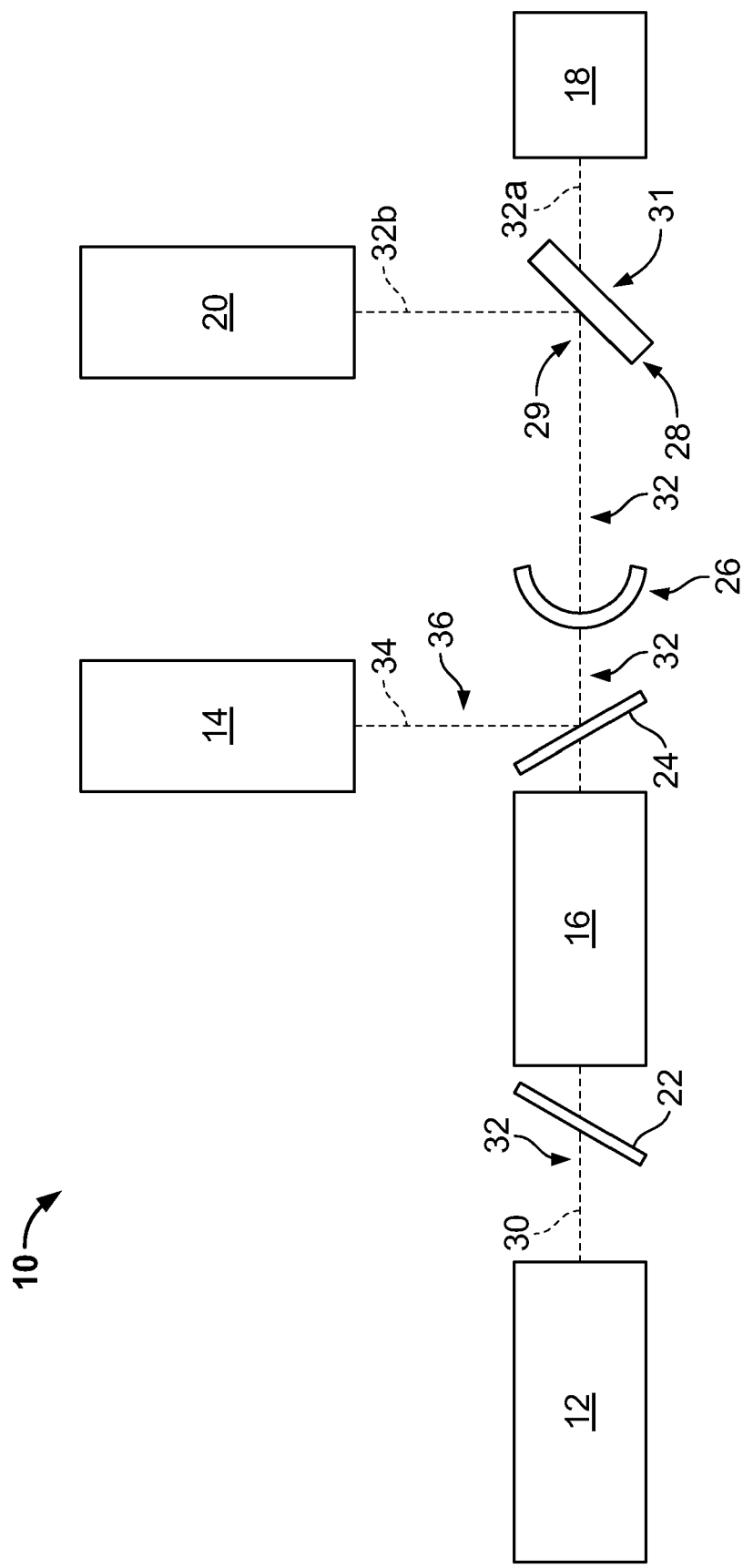
FIG. 2 is a schematic block diagram of the optical gas detector shown in FIG. 1.
Figure 3:
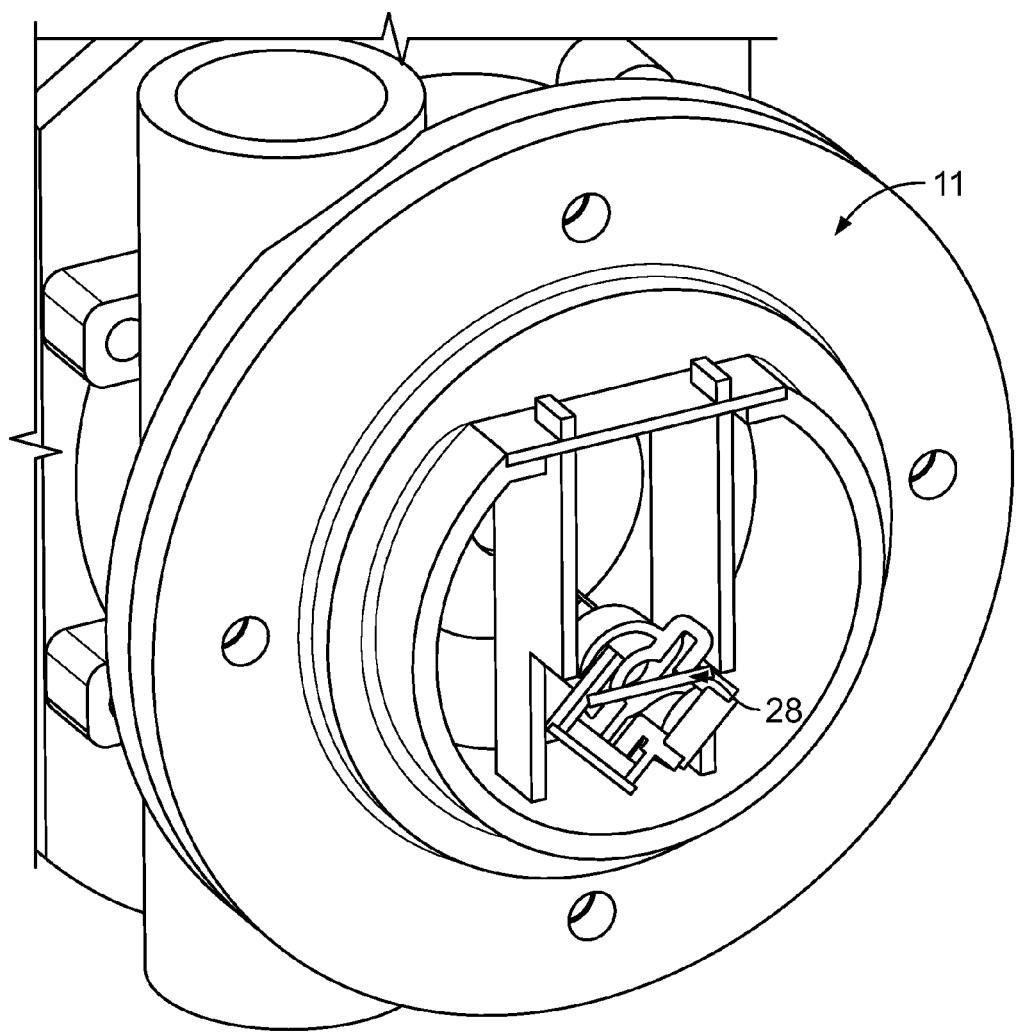
FIG. 3 is a perspective view of an exemplary embodiment of a beam splitter of the optical gas detector shown in FIGS. 1 and 2.
Figure 4:
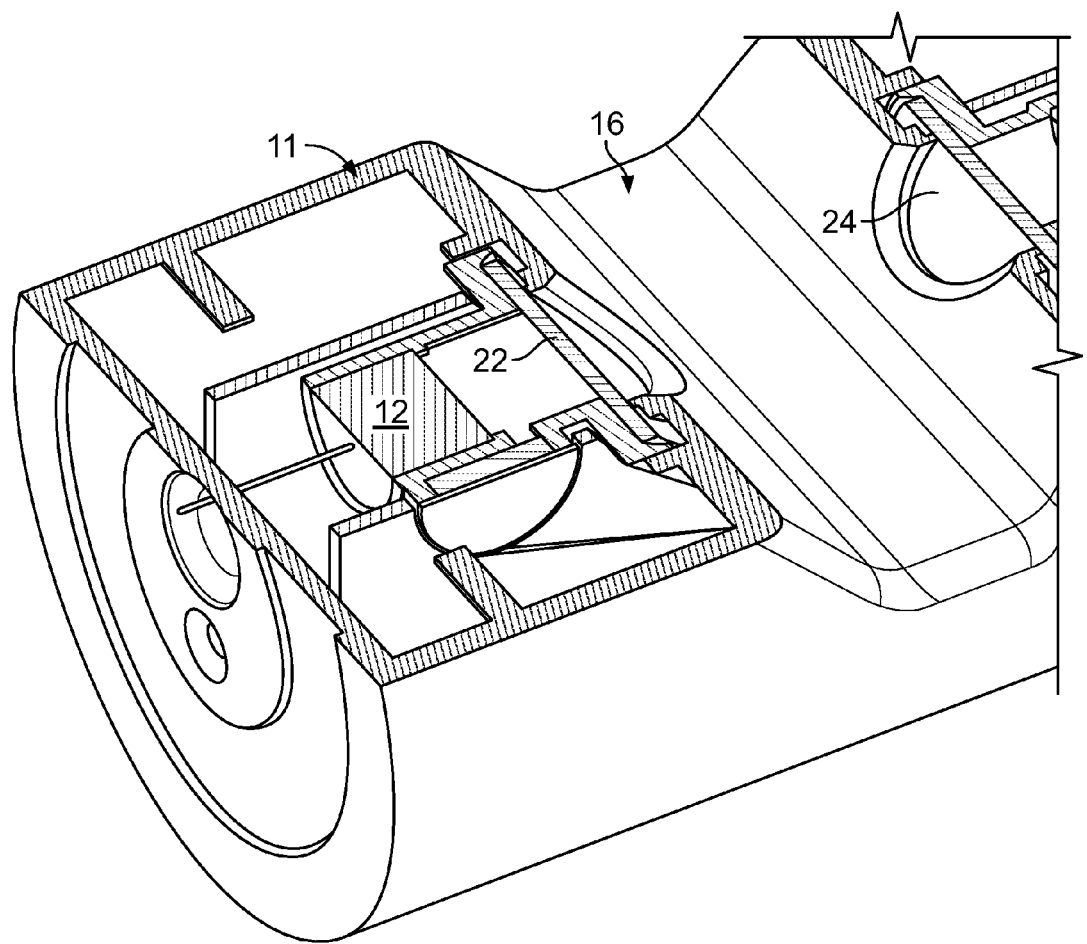
FIG. 4 is a perspective view of an exemplary embodiment of a measurement source of optical radiation of the optical gas detector shown in FIGS. 1 and 2.

FIG. 1 is a perspective view of a cross section of an exemplary embodiment of an optical gas detector 10. FIG. 2 is a schematic block diagram of the optical gas detector 10. FIG. 3 is a perspective view of an exemplary embodiment of a beam splitter 28 of the optical gas detector 10. FIG. 4 is a perspective view of an exemplary embodiment of a measurement source 12 of optical radiation of the optical gas detector 10. The detector 10 includes a body 11 that holds a measurement source 12 of optical radiation, a reference source 14 of optical radiation, a sample region 16 for receiving a gaseous sample, a measurement detector 18, and a reference detector 20. A window 22 is optionally positioned downstream from the measurement source 12 and upstream from the sample region 16 to receive optical radiation emitted from the measurement source 12. The sample region 16 is positioned downstream from the window 22 to receive optical radiation emitted from the measurement source 12 that has traveled through the window 22. As shown in FIG. 1, the sample region 16 is defined by a portion of the body 11 that is open to the ambient environment such that the optical radiation emitted by the measurement source 12 travels through a gaseous sample of the ambient environment. Another window 24 is positioned downstream from the sample region 16 and upstream from the detectors 18 and 20 to transmit optical radiation emitted from the measurement source 12 that has traveled through the sample region 16 and to reflect optical radiation emitted from the reference source 14. Although the window 24 is shown in the exemplary embodiments as being downstream from the sample region 16, the window 24 may alternatively be contained partially within the sample region 16 such that the window 24 is downstream from only a portion of the sample region 16. The windows 22 and 24 are each partially transparent to optical radiation and partially reflective to optical radiation. A collimating lens 26 is optionally positioned downstream from the window 24 and upstream from the detectors 18 and 20 to receive optical radiation emitted from the measurement source 12 that has traveled through the window 22, the sample region 16, and the window 24. As will be described in more detail below, the collimating lens 26 is also positioned to receive optical radiation emitted from the reference source 14 that has been reflected by the window 24.

Figure 7:
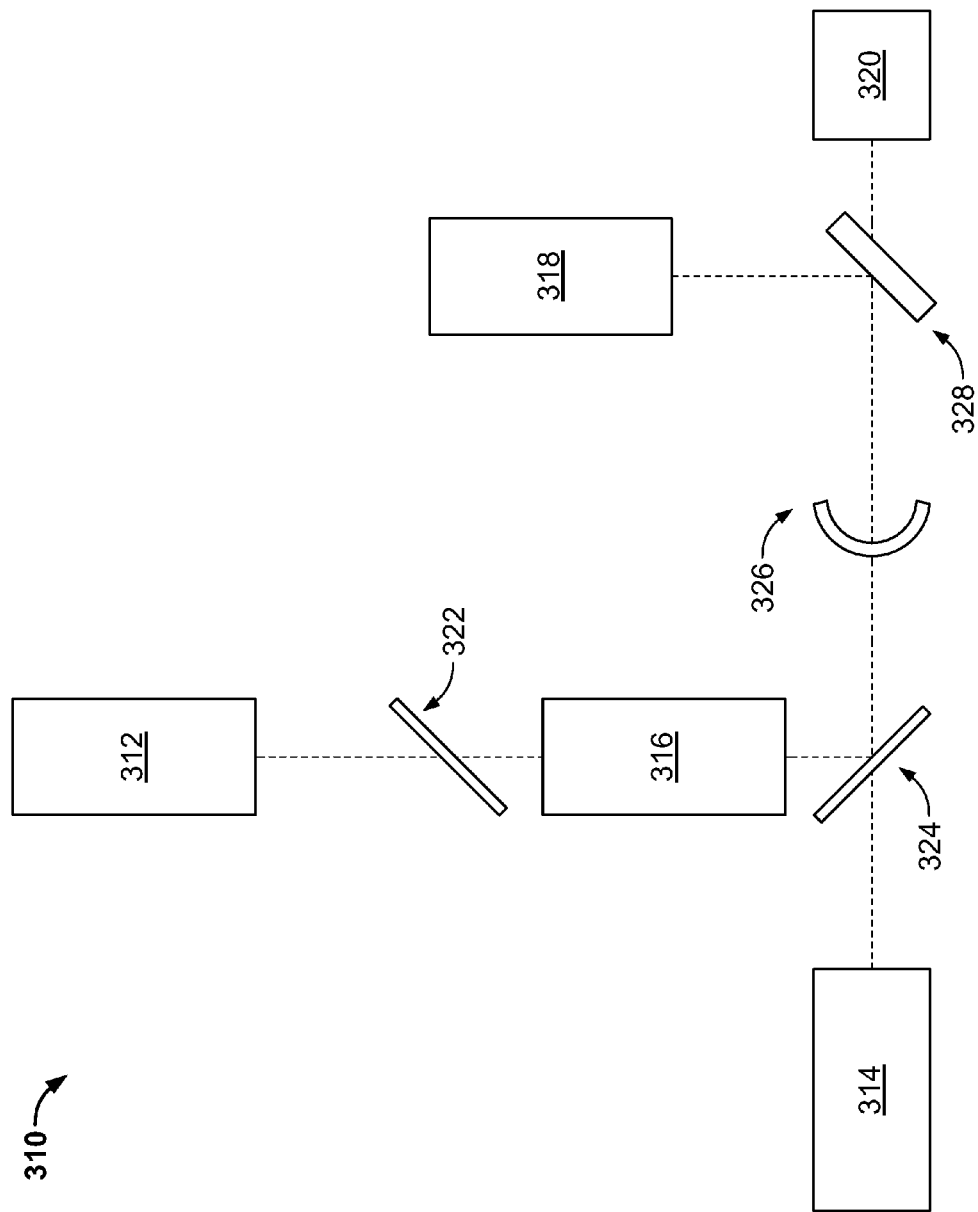
FIG. 7 is a schematic block diagram of an exemplary alternative embodiment of an optical gas detector.

As is shown in FIG. 7, which is described below, the positions of the measurement source 12 and the reference source 14 as shown herein may optionally be reversed, such that the window 24 reflects optical radiation emitted by the measurement source 12 to the collimating lens 26 and such that the collimating lens 26 receives optical radiation emitted by the reference source 14 that has traveled through the window 24.

Referring again to FIGS. 1-4, a beam splitter 28 that is partially transparent to optical radiation and partially reflective to optical radiation is optionally positioned downstream from the collimating lens 26 and upstream from the detectors 18 and 20. The beam splitter includes a side 29 and an opposite side 31. The beam splitter 28 is positioned to receive both optical radiation emitted by the measurement source 12 and optical radiation emitted by the reference source 14 at the same side 29. The measurement detector 18 and the reference detector 20 are both positioned downstream from the beam splitter 28 to receive optical radiation emitted by the measurement source 12 from the beam splitter 28. The measurement detector 18 is configured to provide an output signal indicative of the presence or concentration of a gas of interest, while the reference detector 20 is configured to provide an output signal that is at least partially independent of the gas of interest. As is shown in FIG. 7, which is described below, the positions of the measurement detector 18 and the reference detector 20 as shown herein may optionally be reversed, such that the measurement detector 18 receives reflected optical radiation and the reference source 20 receives optical radiation that has traveled through the beam splitter 28.

Figure 8:
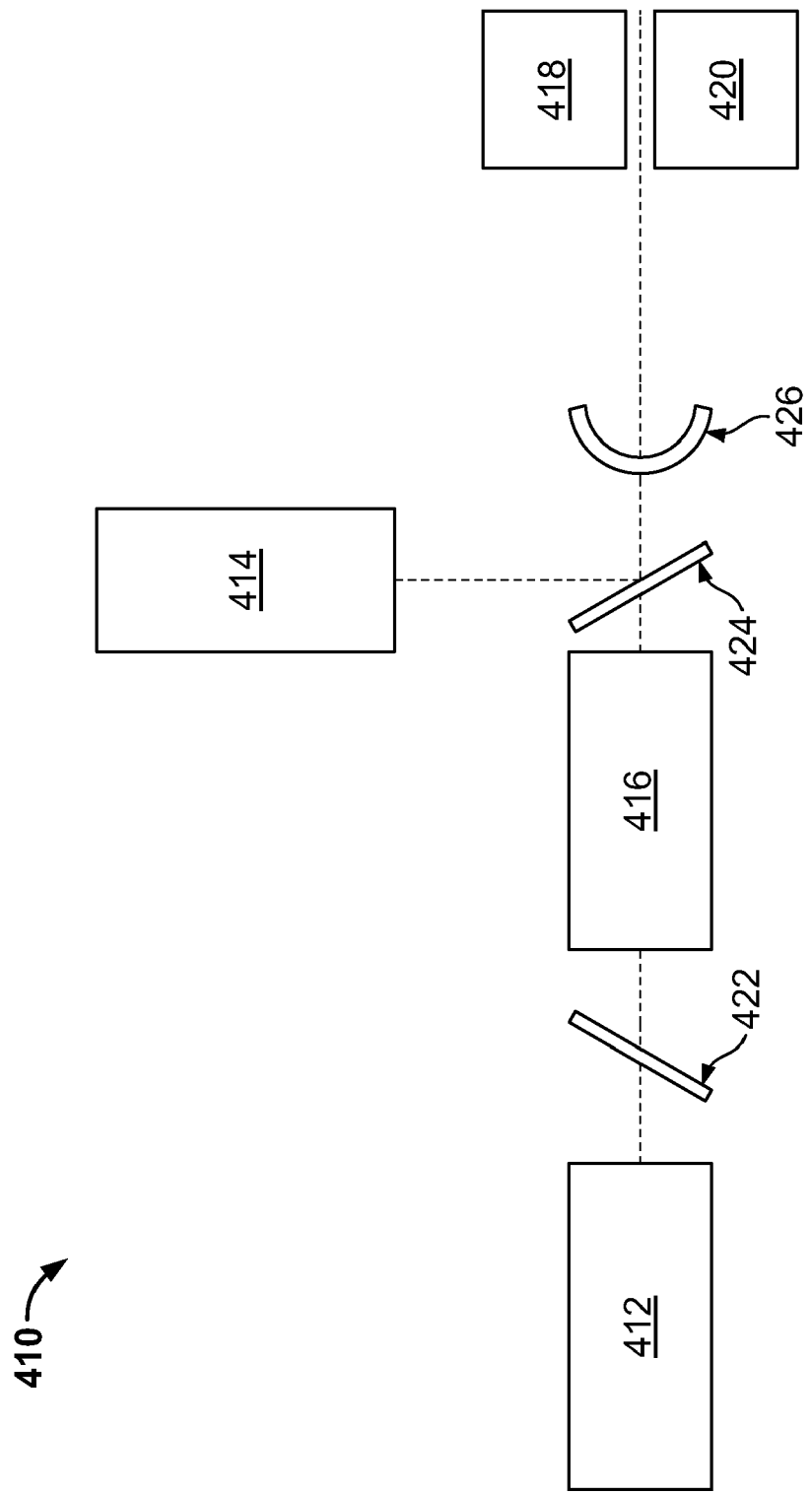
FIG. 8 is a schematic block diagram of an exemplary alternative embodiment of an optical gas detector.

As is shown in FIG. 8, which is described below, the beam splitter 28 may optionally be omitted from the gas detector 10 and the measurement and reference detectors 18 and 20, respectively, may instead by placed approximate one another, such as, but not limited to, using a dual detector.

Referring again to FIGS. 1-4, the measurement source 12 emits optical radiation along an emission axis 30 (FIG. 2). The optical radiation emitted by the measurement source 12 may be referred to herein as measurement radiation. An optical path of the measurement radiation emitted by the measurement source 12 is indicated by the reference numeral 32 (FIG. 2). The optical path 32 may be referred to herein as a measurement optical path. The optical path 32 is defined from the measurement source 12, through the window 22, through the sample region 16, through the window 24, through the collimating lens 26, and to the beam splitter 28. As shown herein, the path of the measurement radiation through the sample region is approximately straight. Alternatively, the path of the measurement radiation through the sample region may not be approximately straight. The beam splitter 28 directs a portion of the measurement radiation to the measurement detector 18, which is indicated by the optical subpath 32a. Another portion of the measurement radiation is directed by the beam splitter 28 to the reference detector 20, which is indicated by the optical subpath 32b. Specifically, the beam splitter is positioned, including a relative angle thereof, relative to the collimating lens 26 and each of the measurement and reference detectors 18 and 20, respectively, to allow a portion of the measurement radiation to pass therethrough while reflecting another portion of the radiation. In the exemplary embodiment, the portion of the measurement radiation that is directed to the measurement detector 18 passes through the beam splitter 28, while the other portion of the measurement radiation is reflected by the beam splitter 28 to the reference detector 20. Alternatively, the beam splitter 28 is positioned relative to the collimating lens 26 and the measurement and reference detectors 18 and 20, respectively, such that the portion of the measurement radiation that is directed to the measurement detector 18 is reflected by the beam splitter 28, while the other portion of the measurement radiation that is directed to the reference detector 20 passes through the beam splitter 28. The beam splitter 28 is configured, including the split ratio, the position, and the angle thereof, to direct a suitably comparable, ideally equal, portion of the measurement radiation to each of the measurement and reference detectors 18 and 20, respectively. However, the split ratio of the beam splitter 28 may change due to contamination (e.g., from dust and/or dirt) and/or a change in ambient conditions, such as, but not limited to, a change in temperature and/or humidity. The change of the split ratio of the beam splitter 28 may cause the portions of the measurement radiation directed to the measurement and reference detectors 18 and 20, respectively, to change from time to time. The split ratio of the beam splitter may be affected by its index of refraction, the ratio of reflective area to transmissive area, polarization effects, and so forth.

The reference source 14 emits optical radiation along an emission axis 34. The optical radiation emitted by the reference source 14 may be referred to herein as reference radiation. An initial portion of the optical path of the reference radiation emitted by the reference source 14 is indicated by the reference numeral 36. The optical path 36 may be referred to herein as a reference optical path. The optical path 36 is defined from the reference source 14 to the window 24. The window 24 is positioned, including a relative angle thereof, relative to the emission axis 34 of the reference source 14 such that the window 24 reflects a portion of the reference radiation to the collimating lens 26. Accordingly, the reference source 14 is positioned to introduce reference radiation into the optical path 32 of the measurement radiation downstream from the sample region 16 such that the reference radiation travels along a portion of the optical path 32 of the measurement radiation that is downstream from the sample region 16. In other words, downstream from the sample region 16, the measurement radiation and the reference radiation follow the same path 32. The remainder of the reference radiation that is not reflected by the window 24 passes through the window 24 to the ambient environment. Similar to that described above with respect to the measurement radiation, after the reference radiation travels through the collimating lens 26, the beam splitter 28 directs a portion of the reference radiation to the measurement detector 18, which is indicated by the optical subpath 32a, and directs another portion of the reference radiation to the reference detector 20, which is indicated by the optical subpath 32b. Accordingly, both the measurement and the reference radiation are transmitted to the same side 29 of the beam splitter 28.

Figure 5:
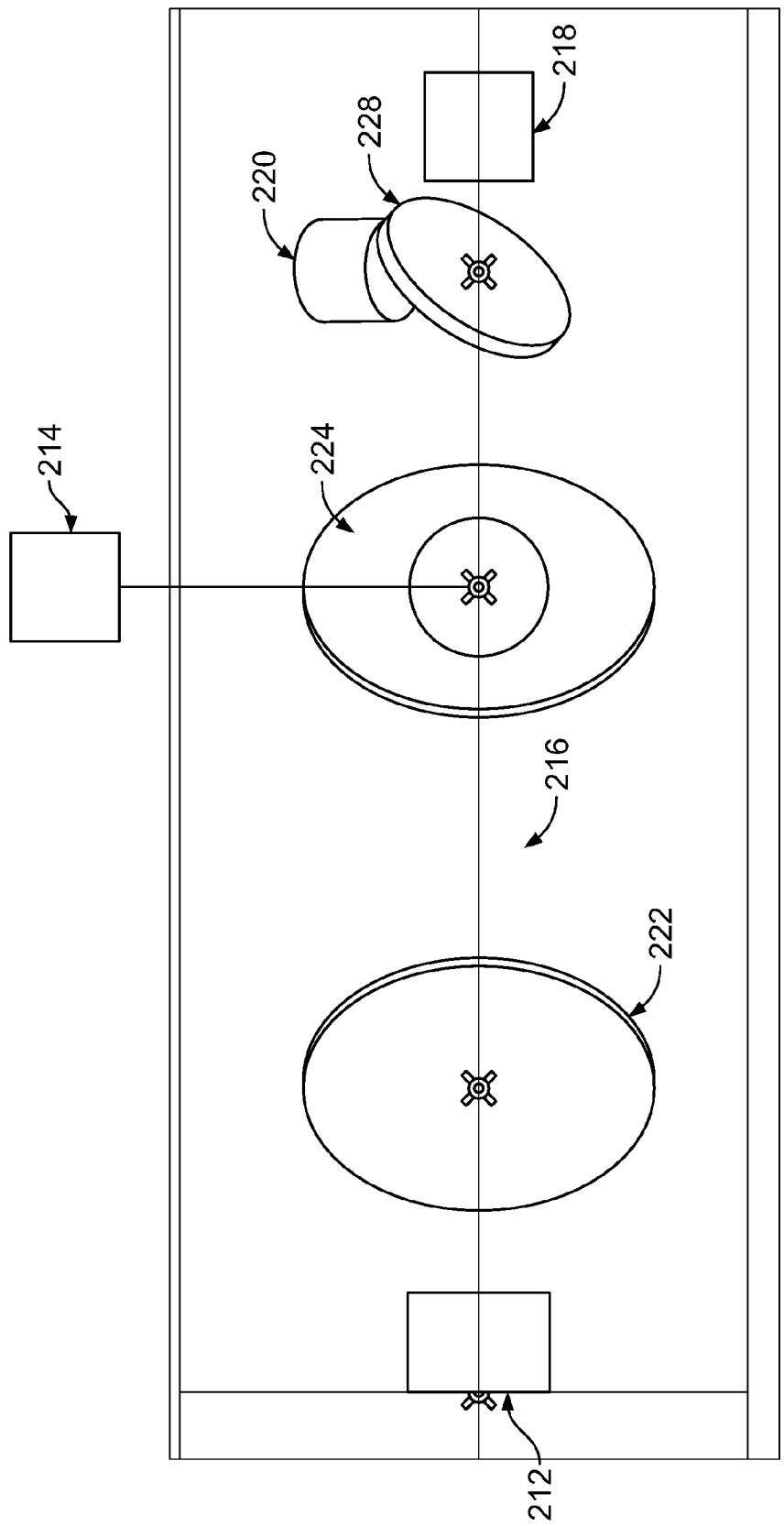
FIG. 5 is a schematic diagram of an exemplary embodiment of an optical gas detector.

Reflecting the reference radiation from the window 24 changes the polarization of the reference radiation. Because the beam splitter 28 may divide incident energy as a function of the polarization of the incident energy, in some embodiments, an alignment of the window 24 and the reference source 14 with respect to the beam splitter 28 and the reference detector 20 may be adjusted to minimize the effect of the difference in polarization between the reference and measurement radiation. For example, in some embodiments, the polarization plane defined by the paths of incident and reflected radiation at the window 24 is rotated about 45 degrees from the polarization plane defined by the paths of incident and reflected radiation at the beam splitter 28. If the beam splitter 28 is refractive, the split ratio changes according to the polarization of incident radiation. When the two polarization planes are separated by 45 degrees on the axis 30 of the ray from the effective center of the measurement radiation source 12 to the effective center of the measurement detector 18, the split ratio of the beam splitter 28 is unaffected by the polarization of the reference radiation on reflection at the window 24. The polarization plane of the window 24 is defined by the ray, as commonly employed in optics analysis, from the axis 34 of the effective center of the reference radiation source 14, incident on the window 24, and reflected to the effective center of the measurement detector 18. The polarization plane of the beam splitter 28 is defined by the ray from the effective center of the measurement radiation source 12, incident on the beam splitter 28, and reflected to the effective center of the reference detector 20. Similar alignment adjustments between the window 24 and the measurement source 12 with respect to the beam splitter 28 and the measurement detector 18 may be made in alternative embodiments (e.g., the detector 310 shown in FIG. 7) wherein the window 24 reflects optical radiation from the measurement source 12. FIG. 5 is a schematic diagram of an optical gas detector 210 wherein a polarization plane defined by the paths of incident and reflected radiation at a window 224 is rotated about 45 degrees from the polarization plane defined by the paths of incident and reflected radiation at a beam splitter 228. The detector 210 includes a measurement source 212 of optical radiation, a reference source 214 of optical radiation, a sample region 216 for receiving a gaseous sample, an optional window 222, the window 224, the beam splitter 228, a measurement detector 218, and a reference detector 320.

Referring again to FIGS. 1-4, although the window 24 is shown as being completely downstream from the sample region 16, the window 24 may alternatively be positioned within or upstream from the sample region 16. If the window 24 is positioned upstream or at the beginning of the sample region 16, such that the optical radiation emitted by both the reference source 14 and the measurement source 12 travel through the entirety of the sample region 16, the measurement source 12 may be separated from the window 24 by a greater distance than the reference source 14.

The window 24 may be regarded as a beam splitter for the optical radiation emitted by the measurement and reference sources 12 and 14, respectively. In the embodiment of FIGS. 1-4, the lower reflectance of the window 24 to the optical radiation emitted by the reference source 14 and the higher transmission of the window 24 to the optical radiation emitted by the measurement source 12 may provide a predetermined split ratio between the closer, more constant, optical radiation emitted by the reference source 14 and the more distant, more variable, optical radiation emitted by the measurement source 12.

The window 24 may be fabricated from any suitable material having any suitable index of refraction, and may have any suitable angle relative to the emission axis 34 of the reference source 14 and the emission axis 30 of the measurement source 12 that enables the window 24 to function as described herein. In the exemplary embodiment, the window 24 is angled at approximately 45° relative to the emission axis 34 of the reference source 14 and the emission axis 30 of the measurement source 12. Moreover, in the exemplary embodiment, the window 24 is fabricated from transparent sapphire. The window 24 may configured, including the index of refraction, the position, and the angle thereof, to reflect any amount of the reference radiation emitted from the reference source 14 to the collimating lens 26. In the exemplary embodiment, the window 24 reflects less than approximately 10% of the reference radiation emitted from the reference source 14 to the collimating lens 26. When the window 24 reflects less radiation than it allows to pass therethrough, the intensity of the measurement radiation transmitted through the collimating lens, and therefore to the detectors 18 and 20, may be greater than the intensity of the reference radiation reference radiation transmitted through the collimating lens, and therefore to the detectors 18 and 20. However, such a difference in intensity may be at least partially equalized, because, at least in part, the reference source 14 may be closer to the window 24 than the measurement source 12. The relative distances of the reference and measurement sources 14 and 12, respectively, to the window 24 may be selected to provide a relatively equal intensity of reference and measurement radiation that is transmitted to the detectors 18 and 20, to whatever degree of equality may be advantageous.

In an alternative embodiment, the window 24 is a wire mesh (not shown) that is formed from one or more wires that at least partially opaque to optical radiation. In such an alternative embodiment wherein the window is a wire mesh, openings between the wires enable at least some of the measurement or reference radiation (depending on the relative positions of the measurement and references sources 12 and 14, respectively) to travel through the window 24 along the optical path 32 while the wires reflect at least some of the other of the measurement and reference radiation into the optical path 32. For example, if the window 24 of the embodiment of FIGS. 1-4 is a wire mesh, at least some of the measurement radiation emitted by the measurement source 12 travels through the window 24 along the optical path 32 while at least some of the reference radiation emitted by the reference source 14 is reflected by the wires into the optical path 32.

The beam splitter 28 may be fabricated from any suitable material having any suitable index of refraction, and may have any suitable angle relative to the optical path 32, the collimating lens 26, and the measurement and reference detectors 18 and 20, respectively, that enables the beam splitter 28 to function as described herein. In the exemplary embodiment, the beam splitter 28 is angled at approximately 45° relative to the optical path 32 and each of the measurement and reference detectors 18 and 20, respectively. Moreover, in the exemplary embodiment, the beam splitter 28 is fabricated from silicon. Silicon has a large index of refraction that produces almost equal reflection and transmission of incident infrared radiation.

Figure 6:
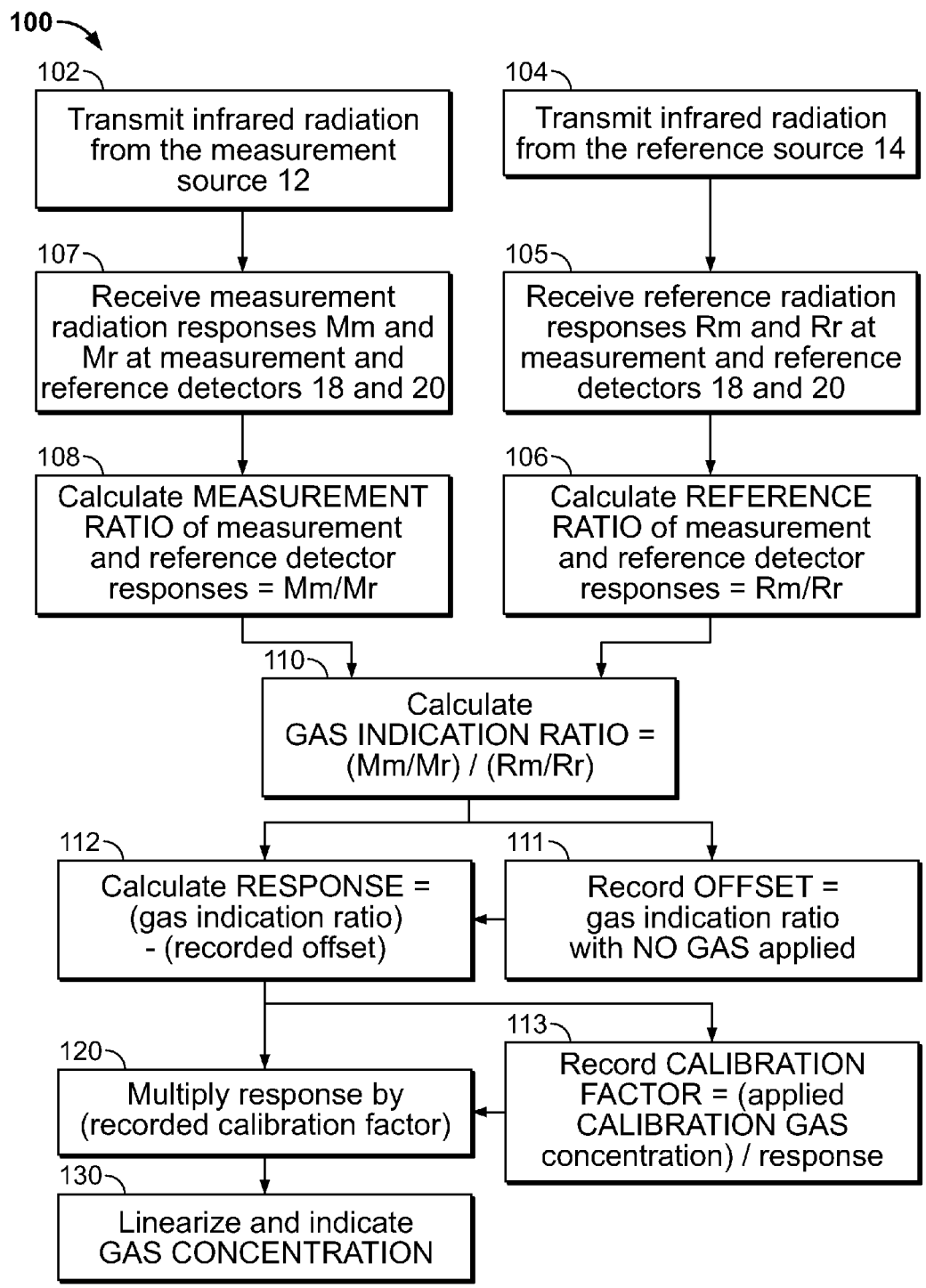
FIG. 6 is a flowchart illustrating an exemplary embodiment of a method for detecting gas using the gas detector shown in FIGS. 1 and 2.

FIG. 6 is a flowchart illustrating an exemplary embodiment of a method 100 for detecting a gas of interest using the gas detector 10 (FIGS. 1 and 2). The method includes transmitting 102 optical radiation from the measurement source 12 (FIGS. 1 and 2), through the window 22 (FIGS. 1 and 2), through the sample region 16 (FIGS. 1 and 2), through the window 24 (FIGS. 1 and 2), through the collimating lens 26 (FIGS. 1 and 2), to the beam splitter 28 (FIGS. 1 and 2), and to the measurement and reference detectors 18 and 20 (FIGS. 1 and 2), respectively. The method 100 also includes transmitting 104 optical radiation from the reference source 14 (FIGS. 1 and 2) to the window 24 such that a portion of the reference radiation is reflected by the window 24 through the collimating lens 26, to the beam splitter 28, and to the measurement and reference detectors 18 and 20, respectively. The measurement and reference radiation may be transmitted 102 and 104, respectively, alternatingly, or may be transmitted 102 and 104, respectively, generally simultaneously. When transmitted 102 and 104 simultaneously, the measurement and reference radiation may be amplitude modulated, where the modulation is phase shifted from one another such that known, phase-detection methods may be employed to distinguish between the reference and measurement radiation sensed by the detectors 18 and 20. Optionally, the modulation frequency of the measurement radiation may be different from the modulation frequency of the reference radiation and known frequency-selective methods may be employed to distinguish between measurement and reference radiation.

Each of the measurement and reference detectors 18 and 20, respectively, thereby receives 107 and 105 two different signals. Specifically, the measurement detector 18 receives a measurement radiation signal Mm and a reference radiation signal Rm, while the reference detector receives a measurement radiation signal Mr and a reference radiation signal Rr. A reference ratio is determined 106 by comparing the reference radiation signal Rm and the reference radiation signal Rr, while a measurement ratio is determined 108 by comparing the measurement radiation signal Mm and the measurement radiation signal Mr. A gas indication ratio is then determined 110 by comparing the reference ratio and the measurement ratio.

An offset, which represents the gas indication ratio when the gas detector 10 is free of the target gas, is then recorded 111. Subsequently, response is calculated 112 as the difference between the gas indication ratio and the recorded offset. A calibration factor is then recorded 113 by dividing a ratio of a known concentration value of gas applied to the gas detector 10 by the calculated 112 response. Subsequently, the response may be multiplied 120 by the recorded calibration factor. The result of the multiplication 120 is an accurate indication of gas concentration.

Optionally, the accuracy of measurement may be improved by a suitable linearization algorithm 130, as is common practice.

As changing ambient conditions change the index of refraction of the beam splitter 28, the split ratio, the ratio between the amount of radiation that is reflected by the beam splitter 28 and the amount of radiation that travels through the beam splitter 28 will also change. However, because the reference detector 20 receives reference radiation and measurement radiation in the same manner (i.e., reflected from or transmitted through the beam splitter 28), and because the measurement detector 18 also receives reference radiation and measurement radiation in the same manner (i.e., reflected from or transmitted through the beam splitter 28), the reference and measurement ratios will change in response to the changing ambient conditions in approximately the same proportion. In other words, a changing split ratio affects reference radiation and measurement radiation by similar proportions. Because the reference and measurement ratios will change in response to the changing ambient conditions by approximately the same amount, ratio between the reference and measurement ratios may be unaffected by the changing ambient conditions.

FIG. 7 is a schematic block diagram of an exemplary alternative embodiment of an optical gas detector 310. The detector 310 includes a measurement source 312 of optical radiation, a reference source 314 of optical radiation, a sample region 316 for receiving a gaseous sample, an optional window 322, a window 324, an optional collimating lens 326, an optional beam splitter 328, a measurement detector 318, and a reference detector 320. The window 324 is positioned such that the window 324 reflects optical radiation emitted by the measurement source 312 to the collimating lens 326 and such that the collimating lens 326 receives optical radiation emitted by the reference source 314 that has traveled through the window 324. Moreover, the measurement detector 318 receives reflected optical radiation from the beam splitter 328 and the reference detector 320 receives optical radiation that has traveled through the beam splitter 328.

FIG. 8 is a schematic block diagram of an exemplary alternative embodiment of an optical gas detector 410. The detector 410 includes a measurement source 412 of optical radiation, a reference source 414 of optical radiation, a sample region 416 for receiving a gaseous sample, an optional window 422, a window 424, an optional collimating lens 426, a measurement detector 418, and a reference detector 420. The window 424 is positioned such that the window 424 reflects optical radiation emitted by the reference source 414 to the collimating lens 426 and such that the collimating lens 426 receives optical radiation emitted by the measurement source 412 that has traveled through the window 424. The measurement and reference detectors 418 and 420, respectively, are placed approximate one another along a common central reception axis 432 such that both the measurement and reference detectors 418 and 420, respectively, receive substantially equal optical radiation emitted by the measurement and reference sources 412 and 414, respectively. In some embodiments, the measurement and reference detectors 418 and 420, respectively, form a dual detector, while in other embodiments the measurement and reference detectors 418 and 420 are separate detectors.

Figure 9:
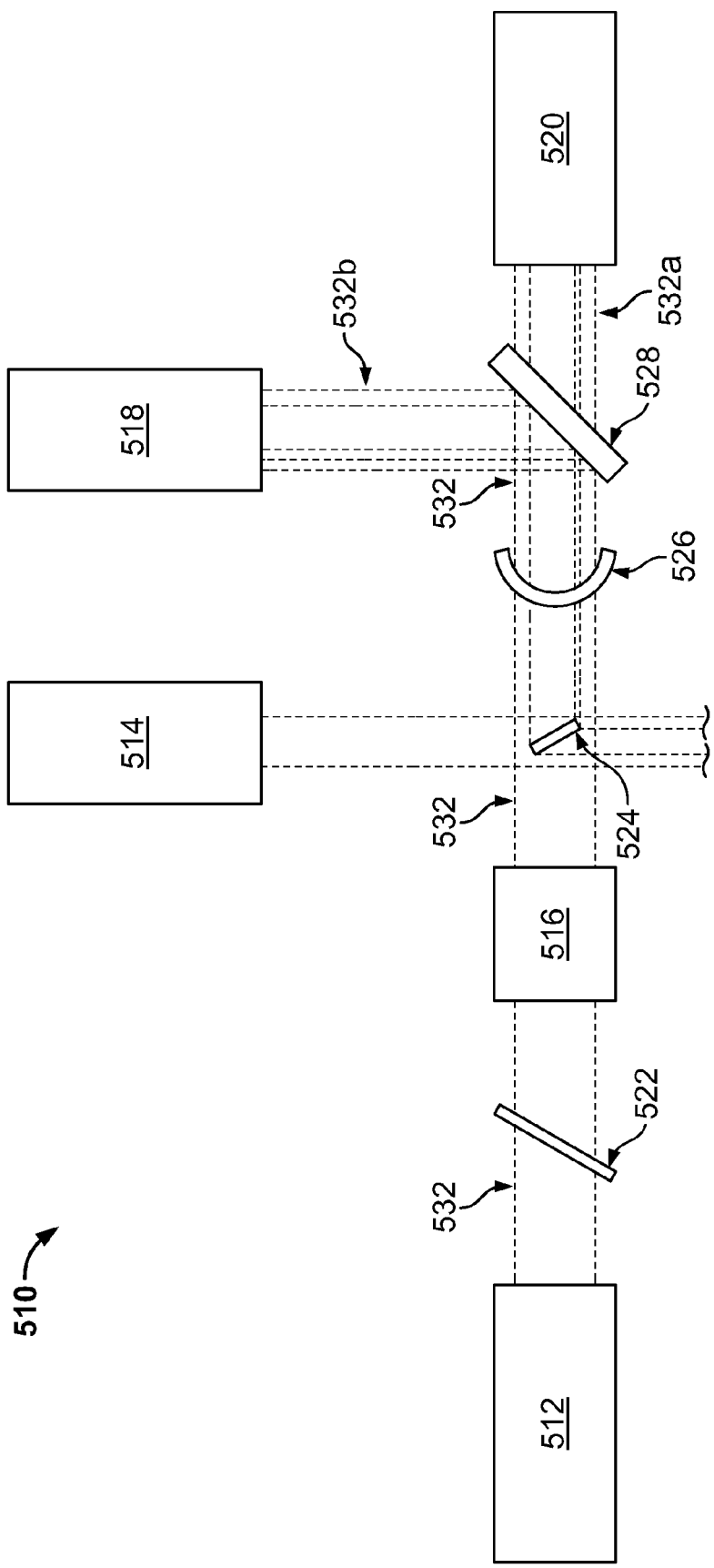
FIG. 9 is a schematic block diagram of an exemplary alternative embodiment of an optical gas detector.

FIG. 9 is a schematic block diagram of an exemplary alternative embodiment of an optical gas detector 510. The detector 510 includes a measurement source 512 of optical radiation, a reference source 514 of optical radiation, a sample region 516 for receiving a gaseous sample, an optional window 522, a reflector 524, an optional collimating lens 526, an optional beam splitter 528, a measurement detector 518, and a reference detector 520. An optical path of the measurement radiation emitted by the measurement source 512 is indicated by the reference numeral 532. The optical path 532 may be referred to herein as a measurement optical path. The optical path 532 is defined from the measurement source 512, through the window 522, through the sample region 516, through the collimating lens 526, and to the beam splitter 528. The reflector 524 is positioned such that the reflector 524 reflects optical radiation emitted by the reference source 514 into the optical path 532. The reflector 524 is also positioned such that the reflector 524 does not block any or blocks only a portion of the measurement radiation emitted by the measurement source 512 from traveling along the optical path 532. The beam splitter 528 directs a portion of the measurement radiation and a portion of the reference radiation to the measurement detector 518, which is indicated by the optical subpath 532a. Other portions of the measurement radiation and the reference radiation are directed by the beam splitter 528 to the reference detector 520, which is indicated by the optical subpath 532b.

As described above, the reflector 524 is positioned such that the reflector 524 does not block any or blocks only a portion of the measurement radiation emitted by the measurement source 512 from traveling along the optical path 532. Specifically, in some embodiments the reflector 524 is positioned in the optical path 532 downstream from at least a portion of the sample region 516 and upstream from the collimating lens 526. When the reflector 524 is positioned in the optical path 532, in some embodiments, and as shown in FIG. 9, the reflector 524 is sized smaller than a cross section of the beam of the measurement radiation emitted by the measurement source 512 such that some of the measurement radiation emitted by the measurement source 512 travels around the reflector 524 and continues along the optical path 532 to the beam splitter 528. Additionally or alternatively to sizing the reflector 524 smaller than a cross section of the beam of the measurement radiation emitted by the measurement source 512, only a portion of the reflector 524 may be positioned in the optical path 532 such that the reflector 524 only blocks a portion of the cross section of the beam measurement radiation and therefore some of the measurement radiation emitted by the measurement source 512 travels around the reflector 524 and continues along the optical path 532 to the beam splitter 528. In another embodiment, the reflector 524 is not positioned in the optical path 532 such that the reflector 524 does not block any of the measurement radiation emitted by the measurement source 512; however, the reflector 524 is positioned and oriented relative to the references source 514 and the optical path 532 to reflect reference radiation emitted by the reference source 514 into the optical path 532 downstream from at least a portion of the sample region 516.

Figure 10:
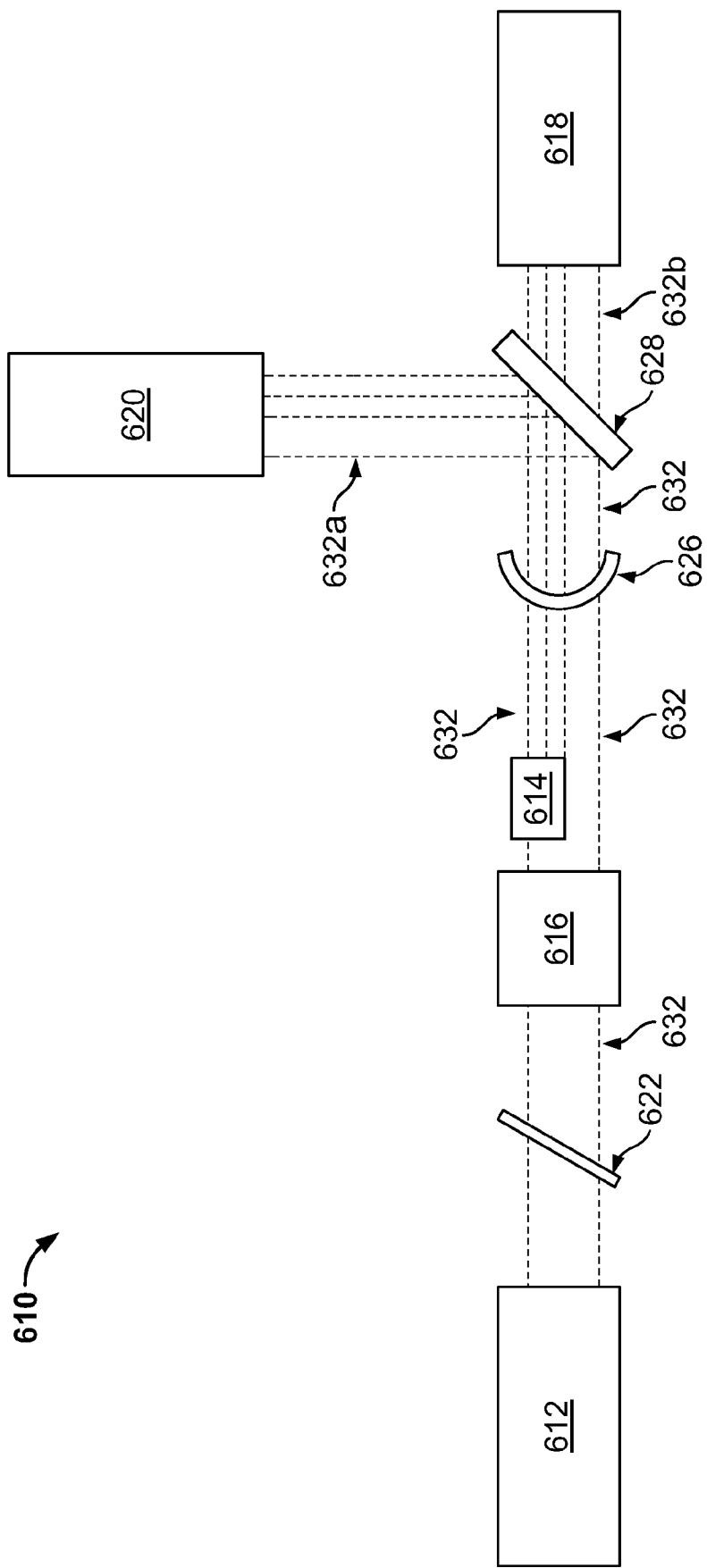
FIG. 10 is a schematic block diagram of an exemplary alternative embodiment of an optical gas detector.

FIG. 10 is a schematic block diagram of an exemplary alternative embodiment of an optical gas detector 610. The detector 610 includes a measurement source 612 of optical radiation, a reference source 614 of optical radiation, a sample region 616 for receiving a gaseous sample, an optional window 622, an optional collimating lens 626, an optional beam splitter 628, a measurement detector 618, and a reference detector 620. An optical path of the measurement radiation emitted by the measurement source 612 is indicated by the reference numeral 632. The optical path 632 may be referred to herein as a measurement optical path. The optical path 632 is defined from the measurement source 612, through the window 622, through the sample region 616, through the collimating lens 626, and to the beam splitter 628. The reference source 614 is positioned such that the reference source 614 introduces optical radiation emitted by the reference source 614 into the optical path 632. The reference source 614 is also positioned such that the reference source 614 does not block any or blocks only a portion of the measurement radiation emitted by the measurement source 612 from traveling along the optical path 632. The beam splitter 628 directs a portion of the measurement radiation and a portion of the reference radiation to the measurement detector 618, which is indicated by the optical subpath 632a. Other portions of the measurement radiation and the reference radiation are directed by the beam splitter 628 to the reference detector 620, which is indicated by the optical subpath 632b.

As described above, the reference source 614 is positioned such that the reference source 614 does not block any or blocks only a portion of the measurement radiation emitted by the measurement source 612 from traveling along the optical path 632. Specifically, in some embodiments the reference source 614 is positioned in the optical path 632 downstream from at least a portion of the sample region 616 and upstream from the collimating lens 626. When the reference source 614 is positioned in the optical path 632, in some embodiments, and as shown in FIG. 10, only a portion of the reference source 614 is positioned in the optical path 632 such that the reference source 614 only blocks a portion of the cross section of the beam measurement radiation and therefore some of the measurement radiation emitted by the measurement source 612 travels around the reference source 614 and continues along the optical path 632 to the beam splitter 628. Additionally or alternatively to positioning only a portion of the reference source 614 in the optical path 632, the reference source 614 may be sized smaller than a cross section of the beam of the measurement radiation emitted by the measurement source 612 such that some of the measurement radiation emitted by the measurement source 612 travels around the reference source 614 and continues along the optical path 632 to the beam splitter 628. In another embodiment, the reference source 614 is not positioned in the optical path 632 such that the reference source 614 does not block any of the measurement radiation emitted by the measurement source 612; however, the reference source 614 is positioned and oriented relative to the optical path 632 to introduce reference radiation emitted by the reference source 614 into the optical path 632 downstream from at least a portion of the sample region 616.

The embodiments described and illustrated herein provide an optical gas detector that may be less sensitive to changing ambient conditions than at least some known optical gas detectors. Moreover, the embodiments described and illustrated herein may provide an optical gas detector having reference and measurement detectors that are substantially identical detector types and/or that operate at substantially the same conditions.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. A gas detector comprising:
a measurement source of optical radiation;
a reference source of optical radiation;
a measurement detector configured to provide an output signal indicative of a gas of interest;
a reference detector configured to provide an output signal at least partially independent of the gas of interest; and
a beam splitter partially transparent to optical radiation and partially reflective to optical radiation, the beam splitter being configured to allow a portion of the optical radiation emitted by both the reference and measurement sources to pass therethrough to one of the measurement detector and the reference detector, the beam splitter being configured to reflect a portion of the optical radiation emitted by both the reference and measurement sources to the other of the measurement and reference detectors.

2. The gas detector according to claim 1, wherein the beam splitter is configured to allow approximately the same amount of optical radiation from the measurement source and the reference source to pass therethrough, and the beam splitter is configured to reflect approximately the same amount of optical radiation from the measurement source and the reference source.

* * * * *